(12) United States Patent
Bosch Cartés et al.

(10) Patent No.: US 7,230,118 B2
(45) Date of Patent: Jun. 12, 2007

(54) PROCESS FOR THE PREPARATION OF ROPINIROLE

(75) Inventors: Joan Bosch Cartés, Barcelona (ES); Xavier Pujol Ollé, Barcelona (ES); José Luis Del Rio Pericacho, Terrassa (ES); Yolanda Alonso Marin, Premià de Mar (ES); Mercè Bessa Sanchez, Vilassar de Mar (ES)

(73) Assignee: Urquima S.A., Palau Solita I Plegamans (ES)

( * ) Notice: Subject to any disclaimer, the term of this patent is extended or adjusted under 35 U.S.C. 154(b) by 0 days.

(21) Appl. No.: 10/572,210

(22) PCT Filed: Oct. 13, 2004

(86) PCT No.: PCT/EP2004/011505

§ 371 (c)(1),
(2), (4) Date: Mar. 17, 2006

(87) PCT Pub. No.: WO2005/040115

PCT Pub. Date: May 6, 2005

(65) Prior Publication Data

US 2007/0032540 A1    Feb. 8, 2007

(30) Foreign Application Priority Data

Oct. 14, 2003    (ES)    ................. 200302382

(51) Int. Cl.
*C07D 209/34*    (2006.01)
*C07D 209/08*    (2006.01)

(52) U.S. Cl. ...................... 548/486; 548/491
(58) Field of Classification Search ............... 548/486, 548/491
See application file for complete search history.

(56) References Cited

FOREIGN PATENT DOCUMENTS

EP    0 113 964 A1    7/1984
WO    WO 9415918 A1 *    7/1994

OTHER PUBLICATIONS

Stjernlof, P., et al., "Structure-Activity Relationships in the 8-Amino-6,7,8,9-tetrahydro-3H-benz[e]indole Ring System. 1. Effects of Substituents in the Aromatic System on Serotonin and Dopamine Receptor Subtypes," *Journal Medical Chemistry*, Jun. 9, 1995, pp. 2202-2216, vol. 38, No. 12.

* cited by examiner

*Primary Examiner*—Kamal A. Saeed
*Assistant Examiner*—Michael P. Barker

(74) *Attorney, Agent, or Firm*—Rothwell, Figg, Ernst & Manbeck

(57) ABSTRACT

A new process for the preparation of Ropinirole (1) and pharmaceutically acceptable hydrochloride salt thereof comprising reacting the compound (V) with nitromethane to obtain the compound of formula (II), which is reduced to compound (III) and alkylated to obtain compound (IV). The oxidation of the indole ring provides the compound of formula (I)

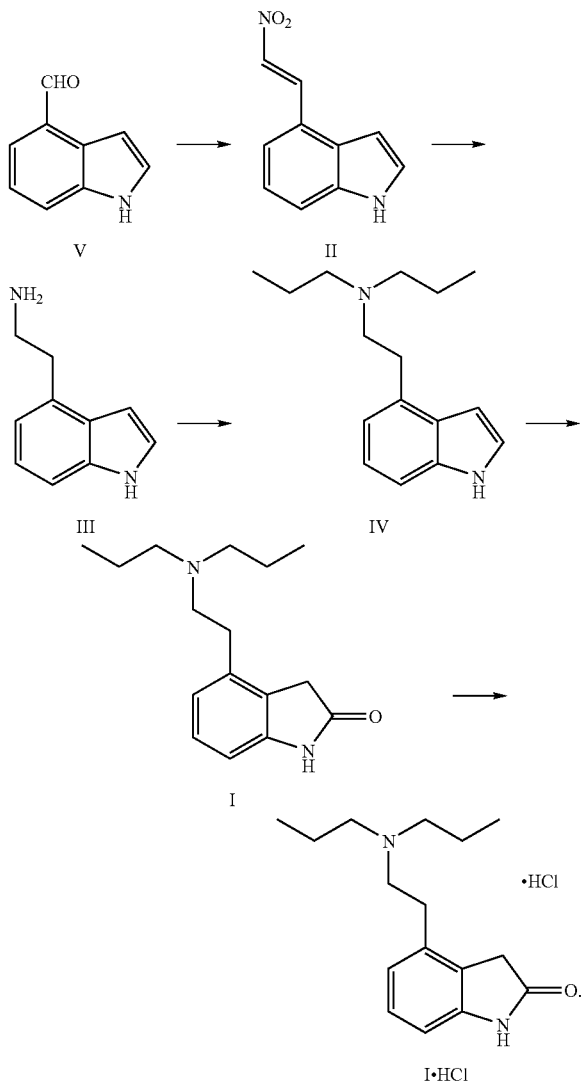

22 Claims, No Drawings

PROCESS FOR THE PREPARATION OF ROPINIROLE

This application is a 371 filing of PCT/EP2004/011505, filed Oct. 13, 2004, which claims priority from Spanish Application 200302382, filed Oct. 14, 2003.

THE SECTION OF TECHNOLOGY WHICH THE INVENTION REFERS TO

The present invention provides a new process for the preparation of Ropinirole useful in the treatment of Parkinson's disease.

DESCRIPTION OF THE TECHNICAL STATUS

The compound 4-[2-(dipropylamino)ethyl]-1,3-dihydro-indol-2-one represented by formula I, commonly known as Ropinirole has been used as an active constituent drug, as the hydrochloride salt.

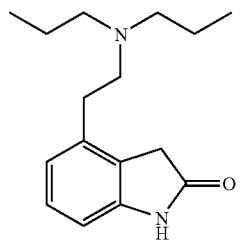

I

Processes for preparing Ropinirole have been described previously. Particularly, the patent number EP-113964 comprising the reduction, using catalytic hydrogenation under low or moderate pressure conditions, of the 2-nitrophenyl acetic acid followed by the cyclization of the intermediate created.

Alternative processes for the preparation of Ropinirole have also been described later on. For example in documents EP-300614 and EP-526529 the reductive cyclization of nitrostyrene compounds carried out in the presence of acetyl chloride and iron chloride is described.

Until now, all processes described for the preparation of Ropinirole have long synthesis or some disadvantages for their application on an industrial scale. For this reason, it is necessary to find an alternative process for the preparation of Ropinirole and/or its pharmaceutically acceptable salts, which are suitable for the preparation at industrial scale.

DESCRIPTION OF THE INVENTION

The present invention provides a process for the preparation of the compound of formula I

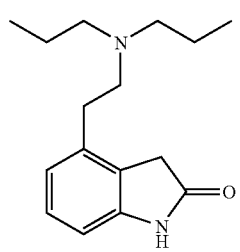

I comprising reacting the compound of formula IV with an oxidising agent.

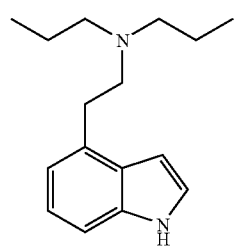

IV

The compound of formula IV can be oxidised by any oxidising agent described in the literature for the conversion of indole into 2-oxindole. The oxidising agent can be selected from the group consisting of halogenating agents such as pyridinium tribromide (PTB), a N-halosuccinimide such as N-chlorosuccinimide (NCS) or N-bromosuccinimide (NBS) in an acidic medium such as acetic acid or hydrochloric acid; or a sulphoxide such as dimethyl sulphoxide (DMSO) or a long chained alkylsulphoxide such as dodecylmethyl sulphoxide or decylmethyl sulphoxide in acidic medium such as for example hydrochloric acid can also be used.

This reaction is carried out in a suitable solvent depending on the oxidising agent, and at a temperature between room temperature and reflux temperature.

In a preferred embodiment of the process, the conversion of IV into I is carried out with pyridinium tribromide (PTB) and in the presence of an acid, preferentially aqueous acetic acid.

In a preferred embodiment, the conversion of IV into I is carried out with N-chlorosuccinimide (NCS) and mineral acid, preferentially aqueous hydrochloric acid.

Later, the compound of formula I can be converted into its pharmaceutically acceptable salts, for example its hydrochloride, by means of the conventional methods already described in the literature as, for example processing with hydrochloric acid.

The compound of formula IV can be prepared by alkylation of the compound III,

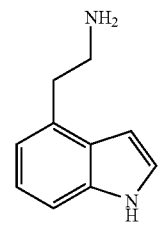

III by reaction with an alkylating agent of formula $CH_3CH_2CH_2$-L, wherein L is a leaving group, optionally in the presence of a base. As a leaving group any group described in the literature can be used, preferably halogen, methanesulphonate, toluenesulphonate, trifluoromethanesulphonate or benzenesulphonate. A wide variety of bases can be used, preferably sodium bicarbonate, potassium bicarbonate, sodium carbonate or potassium carbonate. The reaction is carried out in a suitable solvent, for example toluene.

In a preferred embodiment of the process, the leaving group is halogen and the reaction is carried out in the presence of a base.

In a more preferred embodiment, the leaving group is iodine or bromine and the reaction is carried out in the presence of sodium bicarbonate.

Alternatively the compound of formula IV can be prepared from the compound of formula III, by reaction with a carbonylic compound of formula $CH_3CH_2COR^1$ wherein $R^1$ can be OH or H, in the presence of a reducing agent and in normal reductive amination conditions.

In a preferred embodiment of the process, the carbonylic compound is $CH_3CH_2COR^1$ wherein $R^1$ is OH and the reducing agent is sodium borohydride.

The compound of formula III can be prepared by reducing compound II,

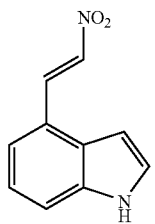

II by reaction with a reducing agent, for example $LiAlH_4$, $NaBH_4$—$BF_3.Et_2O$, $NaBH_4$—$BH_3$, diisobutyl aluminium hydride, bis(2-methoxyethoxy)aluminium hydride or by means of hydrogenation in the presence of a catalyst, for example Pd/C, $Pd(OH)_2$ or $PtO_2.H_2O$.

In a preferred embodiment, the reducing agent is bis(2-methoxyethoxy)aluminium hydride and the reaction is carried out in toluene, tetrahydrofuran or their mixtures at a temperature between room temperature and reflux temperature of the solvent.

The compound of formula II, can be prepared by treatment of 4-indolecarboxaldehyde V

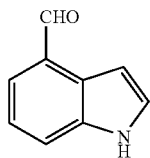

V with nitromethane, in the presence of a base, for example ammonium acetate and optionally in a suitable solvent.

In a preferred embodiment of the process, the compound of formula II can be prepared from compound of formula V by reaction with nitromethane in the presence of ammonium acetate at the reflux temperature of nitromethane.

The compound of formula V, is known and can be prepared by processes already described in the literature, for example the method described by Joseph M. Muchowski in the Journal of Heterocyclic Chemistry 2000, 37(5), 1293.

The following examples are only given by way of illustration of the invention and not to be understood as limiting.

The following abbreviations have been used in the examples:
AcOEt: ethyl acetate
THF: tetrahydrofuran
DIBAH: diisobutyl aluminium hydride

EXAMPLE 1

4-(2-nitrovinyl)indole (II)

Ammonium acetate (5.8 g, 75 mmol) was added to a solution of 4-indolcarboxaldehyde (V) (29 g, 200 mmol) in nitromethane (290 mL), which was stirred and refluxed for 3 h 30 min. The reaction mixture obtained was diluted with AcOEt and washed with a saturated solution of NaCl. The organic layer was dried and concentrated to dryness. The resultant residue was washed with cyclohexane and the solid was filtered, washed and dried under vacuum to obtain, 30.8 g (82%) of 4-(2-nitrovinyl)indole (II).

$^1$H-RMN (200 MHz, DMSO-$d_6$) δ: 6.90 (m, 1H, 3-H), 7.20 (t, J=7.8 Hz, 1H, 2-H), 7.62 (m, 3H, Ar), 8.19 (d, J=14 Hz, 1H, Ar—CH=CH—$NO_2$), 8.42 (d, J=14 Hz, 1H, Ar—CH=CH—$NO_2$), 11.6 (broad, 1H, NH).

EXAMPLE 2

4-[(2-amino)ethyl]indole (III)

Method A:

A solution of 4-(2-nitrovinyl)indole (II) (10 g, 53.2 mmol) in THF (200 mL) was added to a suspension of $LiAlH_4$ (12.1 g, 319.2 mmol) in THF (600 mL) at 0° C. and under inert atmosphere. When the temperature reached room temperature, the reaction mixture was heated at the reflux temperature and stirred at this temperature for 3 hours. Ice-water was added to the resultant suspension, which was filtered through Celite, concentrated and extracted with AcOEt. The organic layer was dried, filtered and concentrated to obtain, 6.9 g (81%) of 4-[(2-amino)ethyl]indole (III).

$^1$H-RMN (200 MHz, $CDCl_3$/$CD_3OD$), δ: 2.06 (broad, 2H, $NH_2$), 3.06 (m, 4H, Ar—$CH_2$—$CH_2$—$NH_2$), 6.55 (m, 1H, 3-H), 6.90-7.30 (m, 4H, Ar), 9.0 (broad, 1H, NH).

Method B:

A solution of 4-(2-nitrovinyl)indole (II) (3 g, 15.9 mmol) in THF (10 ml) was added to a suspension of DIBAH (1M THF, 159 ml, 159 mmol) under an inert atmosphere and was stirred at room temperature for 30 min, then it was heated at 60° C. and stirred for 5 hours. The obtained mixture was cooled to 0° C., AcOEt, water and KOH 10% were added and the ontained product was filtered. The aqueous layer was extracted with AcOEt and the organic layer was dried and evaporated to obtain 4-[(2-amino)ethyl]indole (III).

Method C:

A solution of 4-(2-nitrovinyl)indole (II) (25 g, 132.8 mmol) in THF (325 mL) was added to a solution of bis(2-methoxy)aluminium hydride in toluene 70% (385 g, 1333 mmol) in toluene (325 mL), the reaction mixture was heated to 60-70° C. and at this temperature the THF was distilled. Then toluene (325 mL) was added and stirred at a temperature between 60-70° C. for 2 hours. Once the reaction mixture had reached room temperature, it was cooled to 5-10° C. and then NaOH 5% (600 mL) was slowly added. The organic layer was separated and the aqueous layer was extracted with toluene. The organic layer was washed with HCl 1N and the resultant aqueous layer was basified with NaOH 20% and extracted with toluene to obtain, 13 g (61%) of 4-[(2-amino)ethyl]indole (III).

EXAMPLE 3

4-[2-(dipropylamino)ethyl]indole (IV)

Method A:

NaBH$_4$ (4.8 g, 126.9 mmol) was added to a mixture of 4-[(2-amino)ethyl]indole (III) (4 g, 24.9 mmol) and propionic acid (27.8 mL, 374.4 mmol) under inert atmosphere previously heated at 60° C. and the reaction mixture was stirred at 55-60° C. for 20 hours. When the reaction mixture reached room temperature, NaOH 2N (80 mL) was added and was then washed with toluene. The organic layer was washed with NaOH 2N to obtain, 5.2 g (85%) of 4-[2-(dipropylamino)ethyl]indole (IV).

$^1$H-RMN (200 MHz, CDCl$_3$) δ: 0.91 (t, J=7.3 Hz, 6H, CH$_3$), 1.55 (m, 4H, CH$_2$—CH$_3$), 2.53 (m, 4H, N—CH$_2$—CH$_2$—CH$_3$), 3.0 (m, 4H, Ar—CH$_2$—CH$_2$—N), 6.58 (m, 1H, 3-H), 6.90-7.40(m, 4H, Ar), 8.50 (broad, 1H, —NH.

Method B:

A mixture of 4-[(2-amino)ethyl]indole (III) (2.0 g, 12.48 mmol), 1-iodopropane (8.5 g, 50 mmol), NaHCO$_3$ (2.3 g, 27.4 mmol) in toluene (40 mL) was stirred at reflux temperature for 21 h. NaHCO$_3$ (1.15 g, 13.7 mmol) in water (20 mL) and 1-iodopropane (2.12 g, 12.47 mmol) were added to the resultant mixture and was stirred at the same temperature for 6 h. When the mixture reached room temperature, it was filtered and layers were separated. The organic layer was washed with water (15 mL), dried, filtered and evaporated to obtain 2.53 g (83%) of 4-[2-(dipropylamino)ethyl]indole (IV).

EXAMPLE 4

4-[2-(dipropylamino)ethyl]indol-2-one (I)

Method A:

A solution of pyridinium tribromide 90% (8.72 g, 24.5 mmol) in acetic acid 50% (50 mL) was added to a solution of 4-[2-(dipropylamino)ethyl]indol (IV) (5 g, 20.5 mmol) in acetic acid 50% (100 mL) and was stirred at 50° C. for 3 h. When the resultant mixture reached room temperature, it was stirred at this temperature for 16 h. The reaction mixture was concentrated to obtain an aqueous residue, which was diluted with water (100 mL), basified with an aqueous solution of NaOH 10% and extracted with AcOEt. The organic layer was dried, filtered and concentrated to obtain 4.3 g (81%) of 4-[2-(dipropylamino)ethyl]indol-2-one (I).

$^1$H-RMN (200 MHz, CDCl$_3$) δ: 0.88 (t, 6H, CH$_3$), 1.47 (m, 4H, CH$_2$CH$_3$), 2.44 (m, 4H, NCH$_2$CH$_2$CH$_3$), 2.67 (m, 4H, ArCH$_2$CH$_2$N), 3.50 (s, 2H, 3-H), 6.75-7.18 (m, 3H, Ar)

The compound of formula I was purified and converted into its hydrochloride salt.

Method B:

N-chlorosuccinimide (2.52 g, 18.9 mmol) was added to a solution of 4-[2-(dipropylamino)ethyl]indole (IV) (3 g, 12.28 mmol) in toluene (10 mL) and was stirred at room temperature for 1 h. The resultant mixture was washed with an aqueous solution of NaOH 5% and then an aqueous solution of HCl 1N (30 mL) was added to the organic layer and was heated at reflux temperature for 1 h. When the mixture reached room temperature, the organic layer was separated and the aqueous layer was basified with an aqueous solution of NaOH and extracted with AcOEt. The organic layer was dried, filtered and concentrated to obtain 2.1 g (66%) of 4-[2-(dipropylamino)ethyl]indol-2-one (I), which was purified and converted into its hydrochloride salt.

The invention claimed is:

1. A process for the preparation of Ropinirole of formula I or a pharmaceutically acceptable salt thereof

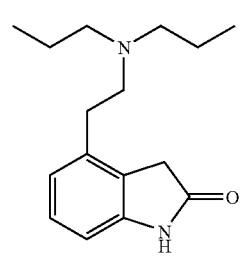

comprising reacting a compound of formula IV

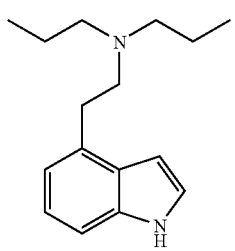

with an oxidizing agent and to form the compound of formula I optionally converting the compound of formula I into a pharmaceutically acceptable salt thereof.

2. A process for the preparation of Ropinirole of formula I or a pharmaceutically acceptable salt thereof

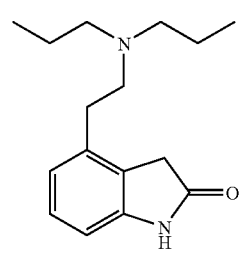

comprising
reacting a compound of formula V

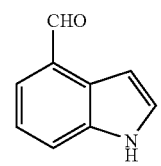

with nitromethane to obtain a compound of formula II

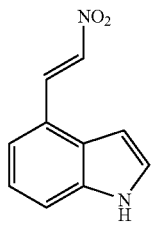

reducing the compound of formula II to obtain a compound of formula III

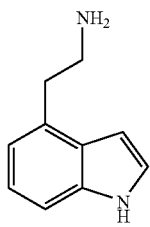

alkylating the compound of formula III to obtain a compound of formula IV

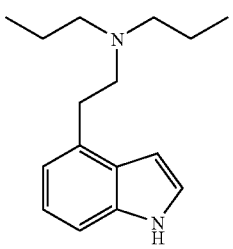

oxidizing the compound of formula IV to obtain the compound of formula I; and optionally converting the compound of formula I into a pharmaceutically acceptable salt thereof.

3. A process according to claim 1 or 2, wherein the oxidising agent is a halogenating agent in an acidic medium.

4. A process according to claim 3, wherein the halogenating agent is pyridinium tribromide of N-halosuccinimide.

5. A process according to claim 1 or 2, wherein the oxidising agent is a sulphoxide in an acidic medium.

6. A process according to claim 5, wherein the sulphoxide is dimethylsulphoxide or a long chained alkylsulphoxide.

7. A process according to claim 1 or 2, wherein the conversion of IV into I is carried out by treatment with pyridinium tribromide in acetic acid and water.

8. A process according to claim 1 or 2, wherein the conversion of IV into I is carried out by treatment with N-chlorosuccinimide in an aqueous mineral acid.

9. A process according to claim 1 or 2, wherein the compound of formula IV is prepared by reacting a compound of formula III

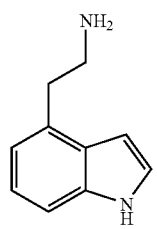

with an alkylating agent of formula $CH_3CHCH_2CH_2$-L, wherein L is a leaving group.

10. A process according to claim 9, wherein the reaction of compound III with the alkylating agent is carried out in the presence of a base.

11. A process according to claim 10, wherein the base is sodium bicarbonate, potassium bicarbonate, sodium carbonate or potassium carbonate.

12. A process according to claim 9, wherein the leaving group L is selected from the group consisting of halogens, methansulphonate, toluenesulphonate, trifluoromethanesulphonate and benzenesulphonate.

13. A process according to claim 9, wherein the leaving group is a halogen.

14. A process according to claim 13, wherein the leaving group L is iodine or bromine.

15. A process according to claim 14, wherein the leaving group L is iodine or bromine and the base is sodium bicarbonate.

16. A process according to claim 1 or 2, wherein the compound of formula IV is prepared by reacting a compound of formula III with a carbonylic compound of formula $CH_3CH_2COR^1$, wherein $R^1$=OH or H and the reaction is carried out in the presence of a reducing agent.

17. A process according to claim 16, wherein $R^1$=OH and the reducing agent is sodium borohydride.

18. A process according to claim 2, wherein the reducing agent is selected from the group consisting of $LiAlH_4$, $NaBH_4$—$BF_3.Et_2O$, Na $BH_4$—$BH_3$, diisobutylaluminum hydride, bis(2-methoxyethoxy)aluminum hydride or hydrogen in the presence of a catalyst.

19. A process according to claim 18, wherein the reducing agent is bis(2-methoxyethoxy)aluminum hydride.

20. A process according to claim 19, wherein the reducing agent is bis(2-methoxyethoxy)aluminum hydride and the reaction is carried out in toluene, tetrahydrofuran or a mixtures thereof at a temperature between room temperature and the reflux temperature of a solvent in which the reaction is carried out.

21. A process according to claim 2, comprising the preparation of the compound of formula II from the compound of formula V

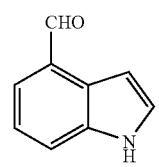

by reaction with nitromethane in the presence of a base.

22. A process according to claim 21, wherein the base is ammonium acetate.

* * * * *